United States Patent [19]

Bonaventura et al.

[11] 4,343,715

[45] Aug. 10, 1982

[54] IMMOBILIZED HEMOGLOBIN, AND PROCESSES FOR EXTRACTING OXYGEN FROM FLUIDS USING THE SAME

[75] Inventors: Joseph Bonaventura; Celia Bonaventura, both of Beaufort, N.C.

[73] Assignee: Duke University, Durham, N.C.

[21] Appl. No.: 196,036

[22] Filed: Oct. 10, 1980

[51] Int. Cl.³ .................. C01B 13/00; A61M 16/00
[52] U.S. Cl. .................................... 252/186; 55/68; 252/188; 423/219; 423/579; 424/177; 435/182
[58] Field of Search .............. 252/188, 186; 128/200, 128/25; 55/68; 423/219, 579; 260/112 B; 424/177; 435/182

[56] References Cited

U.S. PATENT DOCUMENTS

| | | | |
|---|---|---|---|
| 3,925,344 | 12/1975 | Mazur | 424/177 |
| 4,053,590 | 11/1977 | Bonsen et al. | 424/177 |
| 4,061,736 | 12/1977 | Morris et al. | 424/177 |
| 4,064,118 | 12/1977 | Wong | 424/177 |

*Primary Examiner*—Irwin Gluck
*Attorney, Agent, or Firm*—Oblon, Fisher, Spivak, McClelland & Maier

[57] ABSTRACT

An oxygen carrier, capable of reversibly binding and releasing oxygen, immobilized in a polymer matrix and a method of recovering dissolved oxygen from fluids utilizing the same.

9 Claims, 13 Drawing Figures

MATRIX: SIZED-GEL FORMULATION OF HEMOSPONGE
COLUMN: 75ml, 2.26g HEMOGLOBIN
SEAWATER FLOW RATE: 26.5ml/min.
ABSORBED OXYGEN: 2.66mg (62% OF THEORETICAL MAXIMUM)

MATRIX: SIZED-GEL FORMULATION OF HEMOSPONGE
COLUMN: 75ml, 2.26g HEMOGLOBIN
SEAWATER FLOW RATE: 26.5ml/min. WITH 0.25g FERRICYANIDE IN SEAWATER
RELEASED OXYGEN: 1.98mg (46% OF THEORETICAL MAXIMUM)

IMMOBILIZED HEMOGLOBIN, AND PROCESSES FOR EXTRACTING OXYGEN FROM FLUIDS USING THE SAME

This invention was developed under a contract from the Office of Naval Research.

BACKGROUND OF THE INVENTION

1. Field of the Invention

This invention relates to a material for and a process of extracting oxygen from fluids, e.g., gases and natural waters, such as, in which the oxygen is dissolved.

2. Description of the Prior Art

One of the primary problems which hinders man in his efforts to explore and develop the ocean realms is the lack of a ready supply of oxygen. In most of the world's oceans, the oxygen content of both shallow and deep waters is similar to that of surface water in equilibrium with air. Practical methods have not yet been devised for extracting and utilizing this vast amount of oxygen for the maintenance of man in an undersea environment. Fish, however, have obviously solved the problem of oxygen extraction from seawater. Fish species weighing well over a thousand pounds and burning metabolities at rates roughly comparable to that of man easily extract adequate dissolved oxygen from seawater for their varied activities. Moreover, many species of fish transfer oxygen from seawater into a gaseous state. These fish, ones that possess swim bladders, are able to pump and concentrate oxygen against enormous hydrostatic pressure gradients. In certain fish species oxygen is transported from the dissolved state in seawater, with a $pO_2$ of 0.2 atmospheres, to a gaseous phase in the swim bladder where the $pO_2$ may exceed 100 atmospheres. The transfer of oxygen from the seawater to the swim bladder is made possible by the presence of specialized hemoglobin molecules in fish erythrocytes. These specialized hemoglobin molecules-called Root effect hemoglobins- act as miniature molecular pumps. The driving force for such a pump is metabolically produced lactic acid and various organic phosphate cofactors. However, we cannot directly mimic these biological systems, since the hemoglobin is circulated in the blood and is consequently not in a form which can be easily manipulated in large scale flow systems. Many attempts to develop methodologies of extracting oxygen from gaseous mixtures or water are known. Warne et al, U.S. Pat. No. 2,217,850, and Fogler et al, U.S. Pat. No. 2,450,276, disclose processes of separating oxygen from other gases using solutions of cobalt compounds. However, these techniques would be ineffective in a liquid system, e.g., seawater, since the compounds are in solution and would be washed away. Miller, U.S. Pat. No. 3,230,045, discloses using oxygen-binding chromoproteins such as hemoglobin and hemocyanin to separate oxygen from other gases. The chromoproteins are kept moist or in solution and are immobilized on filter paper where they may be bound by a binder such as fibrin, and an electrolyte such as sodium chloride may be present. However, this technique would also be ineffective in a liquid system since the protein is not insoluble and thus would be washed away if water was allowed to flow through the system. Moreover, there is no provision for regeneration of oxidized (inactive) oxygen carriers. Bodell, U.S. Pat. No. 3,333,583, and Robb, U.S. Pat. No. 3,369,343, disclose apparatus for extracting oxygen from seawater using thin tubes of silicone rubber or membrane of silicone rubber, respectively. However, neither the capillary networks nor the permeable membranes have been found to be practicable in real-life situations. Isomura, U.S. Pat. No. 3,377,777, discloses concentrating oxygen from natural waters by equilibration with exhaled gases, i.e. by utilizing large areas of gas-water interface and simple diffusional considerations such that the partial pressure of the gas phase and the partial pressure of the liquid phase in the extraction zone provide for release of oxygen from the liquid phase into the gas phase and absorption of $CO_2$ by the water phase. Additionally, the solubility of oxygen in seawater is decreased by heating the seawater and this heating also increases the solubility of $CO_2$. However, the heating of the seawater produces an energetically undesirable process. Rind, U.S. Pat. No. 4,020,833, discloses an oxygen source for closed environments comprising a mixture of a metallic superoxide, which releases oxygen upon contact with $CO_2$ and water vapor, and a material which absorbs $CO_2$. However, this system suffers from the defect of the capacity being limited by the bulk amount of mixture which can be carried. Iles et al, U.S. Pat. No. 4,165,972, discloses separating oxygen from gas mixtures using metal chelates as sorbents. However, the technique is not extendable to the extraction of oxygen from water.

Many compounds in solution have been examined with respect to their oxygen absorption properties and the mechanistics thereof. The properties of hemoglobins, hemerythrins and hemocyanins, the naturally occurring oxygen carriers, have been the subject of numerous studies, as documented in Bonaventura et al, J. Am. Zool., 20, 7 [1980] and 20, 131 (1980). Artificial oxygen carriers and their properties in solution are described by a number of researchers. Traylor et al, "Solvent Effects on Reversible Formation and Oxidative Stability of Heme-Oxygen Complexes", J.A.C.S., 96, 5597 (1974) discloses the effect of solvent polarity on oxygenation of several heme-base complexes prepared by reduction with sodium dithionite or a mixture of Pd black and calcium hydride. Crumbliss et al, "Monomeric Cobalt-Oxygen Complexes", Science, 6, June 1969, Volume 164, pp. 1168–1170, discloses Schiff base complexes of Co(II) which form stable cobalt-oxygen species in solution instead of cobalt-oxygen-cobalt bridged complexes. Crumbliss et al, "Monomeric Oxygen Adducts of N,N'-Ethylenebis (acetylacetoniminato) ligand-cobalt(II). Preparation and Properties" J.A.C.S. 92, 55 (1970), discloses a series of monomeric molecular oxygen carriers based on cobalt ligand complexes. Dufour et al, "Reaction of Indoles with Molecular Oxygen Catalyzed by Metalloporphyrins", Journal of Molecular Catalysis (In Press), discloses the catalysis of the oxygenation of simple, alkyl-substituted indoles by Co(II), Co(III), and Mn(III) meso-tetraphenyl-porphins wherein a ternary complex $O_2$-CoTPP-indole is formed initially. Brault et al, "Ferrous Porphyrins in Organic Solvents. I. Preparation and Coordinating Properties", Biochemistry, 13, 4591 (1974), discloses the preparation and properties of ferrous deutereporphyrin dimethyl ester and ferrous meso-tetraphenylporphin in various organic solvents. Chang et al, "Kinetics of Reversible Oxygenation of Pyrroheme-N-[3-(1-imidazolyl)propyl] amide", discloses studies on the oxygenation of pyrroheme-N-[3-(1-imidazolyl)propyl] amide, i.e. a synthesized section of the myoglobin active site. Castro, "Hexa and Pentacoordinate Iron Poryhyrins", Bioinorganic Chemistry, 4, 45–65 (1974), discloses the direct synthesis of hexa and pentacoordinate iron porphyrins, i.e. the prosthetic groups for the active sites of certain cytochrome and globin heme proteins. Chang et al, "Solution Behavior of a Synthetic Myoglobin Active Site", J.A.C.S., 95, 5810 (1973), discloses studies on a synthesized section of the myoglobin active site and indicates that the oxygen binding reaction does not require the protein. Naturally occurring oxygen carriers have been chemically cross-linked and their properties described. Bonsen et al, U.S. Pat. No. 4,053,590, discloses a polymerized, cross-linked, stromal-free, hemoglobin proposed to be useful as a blood substitute. Morris et al, U.S. Pat. No. 4,061,736, discloses intramolecularly cross-linked, stromal-free hemoglobin. Wong, U.S. Pat. No. 4,064,118, discloses a blood substitute or extender prepared by coupling hemoglobin with a polysaccharide material. Mazur, U.S. Pat. No. 3,925,344, discloses a plasma protein substitute, i.e. an intramolecular, cross-linked hemoglobin composition. However cross-linked hemoglobin produces macromolecular complexes that retain many of hemoglobin's native properties. The cross-linking of hemoglobin results in a product that is a solution or a dispersion, is not manipulable or, in fact, insolubilized. Large scale flow-thru systems where volumes of water must flow by or through an oxygen extracting medium cannot use hemoglobin which has been crosslinked because the hemoglobin is not truly insoluble. In other words, crosslinking does not accomplish a useful insolubilization, in that, even after crosslinking, the protein in its final form has the characteristics of a fluid.

Numerous papers have been published on immobilization of hemoglobin and its functional consequences, but not in connection with processes for efficient oxygen extraction from fluids. Vejux et al, "Photoacoustic Spectrometry of Macroporous Hemoglobin Particles", J. Opt. Goc. Am., 70, 560–562 (1980), discloses glutaraldehyde cross-linked hemoglobin and its functional properties. The preparation is described as being made up of macroporous particles. Hallaway et al, "Changes in Conformation and Function of Hemoglobin and Myoglobin Induced by Adsorption to Silica", BBRC, 86, 689–696 (1979), discloses that hemoglobin adsorbed on silica is somewhat different from hemoglobin in solution. The adsorbed form is not suitable for $O_2$ extraction from liquids. Antonini et al, "Immobilized Hemoproteins", Methods of Enzymology, 44, 538–546 (1976), discloses standard immobilization techniques as applied to hemoglobin and their functional consequences. Mention is made of hemoproteins bound to cross-linked insoluble polysaccharides such as Sephadex or Sepharose, using a pre-activation of the resin with CNBr. Rossi-Fanelli et al, "Properties of Human Hemoglobin Immobilized on Sepharose 4B", Eur. J. Biochemistry, 92, 253–259 (1978), discloses that the ability of the hemoglobin to be bound to Sepharose 4B is dependent upon the conformational state of the protein. Colosimo et al, "The Ethylisocyanate (EIC) Equilibrium of Matrix-Bound Hemoglobin", BBA, 328, 74–80 (1973), discloses Sephadex G-100, Sephadex DEAE-A50 and Sephadex CM-C50 as supports for human hemoglobin insolubilization. The paper shows that the affinity of the insolubilized protein for EIC is increased relative to that in solution. Lampe et al, "Die Bindung von Sauerstoff an tragerfixiertes Hamoglobin", Acta Biol. Med. Germ., 33, K49–K54 (1974), discloses studies on CM-Sephadex insolubilized hemoglobins. Lampe et al, "Der Einfluß der Immobilisierung von Hamoglobin auf dessen Sauerstoffindung", Acta Biol. Med. Germ., 34, 359–363 (1975), discloses studies on CM-Sephadex insolubilized hemoglobins. Pommerening et al, "Studies on the Characterization of Matrix-Bound Solubilized Human Hemoglobin", Internationales Symposium uber Struktur und Funktion der Erythrozyten (Rapoport and Jung, ed.), Berlin Akademie-Verlag Press, 179–186 (1975), discloses Sepharose-Sephadex types of insolubilization. Brunori et al, "Properties of Trout Hemoglobin Covalently Bound to a Solid Matrix", BBA, 494(2), 426–432, discloses Sepharose 4B or Sephadex G-200, activated by CNBr, to immobilize the hemoglobin. Some changes in the functional properties of the hemoglobin were found.

As may be discerned, there are generally two classes of "insolubilized" hemoglobins described in patents or in open literature. First, cross-linked hemoglobin, e.g., as by glutaraldehyde. Biodegradation of such forms of insolubilized hemoglobin would be rapidly accomplished by the microorganisms in seawater. Nor has full functionality been demonstrated in published accounts. This does not mean that functional properties are necessarily eliminated, but, that methods as described are not suitable for achieving an immobilized form with unimpaired function. Second, Sephadex or Sepharose bound hemoglobins. Low hemoglobin content per volume (specific capacity) makes these methods of insolubilization untenable for large scale use. Biodegradation problems are also present. Additionally, it is not generally possible to achieve high flow rates through such materials.

Various techniques for the insolubilization (or immobilization) of biological materials have been developed, though not described in conjunction with insolubilization and utilization of oxygen carriers. Stanley, U.S. Pat. No. 3,672,955, discloses a technique for the preparation of an insoluble, active enzyme, a biological catalyst, wherein an aqueous dispersion of the enzyme is emulsified with an organic polyisocyanate, mixed with a solid carrier and the volatile components are then evaporated from the mixture. Wood et al, U.S. Pat. No. 3,928,138, discloses a method of preparing a bound enzyme wherein, prior to foaming, an isocyanate-capped polyurethane is contacted with an aqueous dispersion of enzyme under foam-forming conditions, whereby polyurethane foams containing integrally bound enzyme are obtained. Unsworth et al, U.S. Pat. No. 3,928,230, discloses the encapsulation of fluids and solids by dissolving a water-insoluble polymerizable epoxy monomer in a solvent having high affinity for water; dispersing the monomer solution in water; dispersing in the so-formed aqueous dispersion the substance to be encapsulated; adding a polymerizing agent in a solvent having a higher affinity for water than for the polymerizing agent; and polymerizing until polymerization of the monomer is complete. Wood et al, U.S. Pat. No. 3,929,574, discloses an enzyme integrally bound to a foamed polyurethane parepared by, prior to foaming, contacting an isocyanate-capped polyurethane with an aqueous dispersion of enzyme under foam-forming conditions, whereby polyurethane foams containing integrally bound enzyme are obtained. Hartdegen et al, U.S. Pat. No. 4,094,744, discloses water-dispersible protein/polyurethane reaction products formed by admixing a water-dispersible, biologically-active protein and an isocyanate-capped liquid polyurethane prepolymer having a linear polyester backbone under essentially anhydrous conditions to form a solution, said protein and prepolymer reacting to form a water-soluble reaction product wherein the protein and prepolymer are bound together. Hartdegen et al, U.S. Pat. No. 4,098,645, discloses enzymes immobilized by the process of mixing the protein and an isocyanate-capped liquid polyurethane prepolymer in the absence of water; foaming the mixture by reacting it with water to form a polyurethane foam. Huper et al, U.S. Pat. No. 4,044,196, discloses proteins insolubilized using polymers containing maleic anhydride or di- and polymethacrylates. Huper et al, U.S. Pat. No. 3,871,964, discloses proteins insolubilized using polymers containing anhydride, di-methacrylate and a hydrophilic monomer. However, there is no disclosure in the art of an effective way to insolubilize hemoglobin or other oxygen carriers at high concentrations so as to render them active, insoluble and manipulable.

A need therefor continues to exist for not only improved methods for insolubilizing hemoglobin or other oxygen carrying compounds but also for a method of extracting the available dissolved oxygen from natural waters and other fluids. Such methods as will be described will also be useful for preparing blood substitutes which are capable of reversible oxygen binding under physiological conditions.

SUMMARY OF THE INVENTION

Accordingly, one object of the invention is to provide an insolubilized oxygen carrier which is effective for the extraction of oxygen from fluids, e.g., gases and natural waters, such as seawater.

A further object of the invention is to provide an oxygen carrier in a form such that oxygen can be carried from regions of high concentration, such as the lungs, and unloaded in regions of low concentration, such as the respiring tissues.

Briefly, these objects and other objects of the invention as hereinafter will become more readily apparent can be attained by providing oxygen carriers which have been insolubilized at high concentration by being entrapped and/or covalently linked to a polyurethane matrix or to comparable supports in states that are capable of reversible oxygen binding and are regenerable in the event of oxidation.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

This invention relates to the incorporation of an oxygen carrier, which can be a biological macromolecule, into an insolubilized form, which can be a polymeric matrix. More particularly, the preferred embodiment of the invention involves a biochemical engineering technique known as molecular entrapment. The oxygen carrier used by man and other mammals, as well as by most other vertebrates, is hemoglobin. By molecular entrapment, hemoglobin can be made insoluble and consequently more amenable for use in a recycling and regenerable system. Optimally, entrapment is analogous to placing a cage around the biologically active material. This cage, or network, entraps the material but does not render it inactive. The entrapment insolubilizes the material and renders it amenable to manipulation. The degree to which function is maintained varies greatly with the type of entrapment process used. In the preferred polyurethane matrices of this invention, the material retains essentially full biological activity. The preferred material for hemoglobin insolubilization is a hydrophilic polyurethane. The word polyurethane is all-inclusive and is used for all polymers containing urethane linkages. Most polyurethane foams do not have as their starting point a water soluble component, and consequently are not compatible with most biological materials. A special kind of polyurethane prepolymer, one which polymerizes when in contact with water, is required to create the material designated as the preferred embodiment of this invention. In FIGS. 1–3 and 6–11, the insolubilized oxygen carrier is referred to as Hemosponge. Polymerization and insolubilization of the oxygen carrier is effected by adding water to the pre-polymer. The hydrophilic urethane prepolymer which was used to create the Hemosponge described here was developed by W. D. Grace and Company and is the commercially available material HYPOL. Other urethane monomers compatible with the water soluble nature of hemoglobin can be synthesized and these other materials may be used in creation of Hemosponge. The means by which such hydrophilic foams can be synthesized have been published and are in the public domain. The advantages of this technique are numerous. Hemoglobin in such polyurethane foams or gels can be entrapped in high concentrations, the matrix having a variable degree of reticulation. The matrix in the formulations described herein is durable and amenable to all sorts of mechanical manipulation. It can be formed into virtually any configuration. It can be cut, machined, drilled, etc. Even more importantly, in the form of a sponge or sized-gel particles, it has very good diffusional and fluid-flow characteristics.

Figure 1:
FIG. 1 is a 40× magnification showing the nature of a polyurethane reticulated matrix in which hemoglobin is incorporated.
Figure 2:
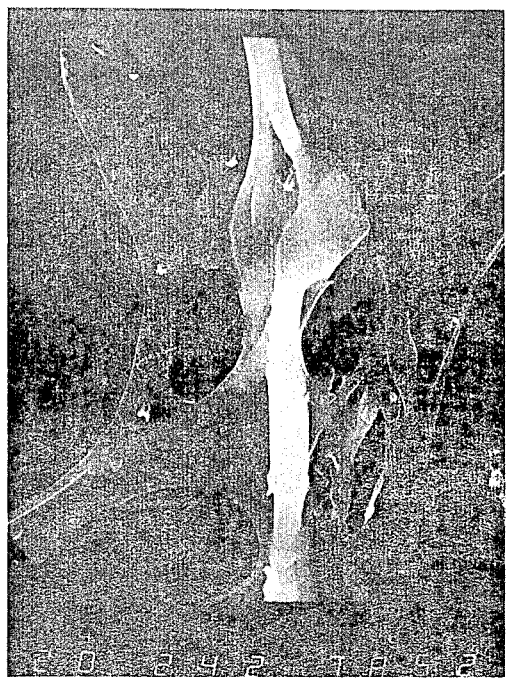
FIG. 2 is a 2400× magnification of the thin walls of the matrix of FIG. 1 at a region of contact between two of the oval compartments.
Figure 3:
FIG. 3 is a 4000× magnification showing the rippled surface of the thin walls of the matrix of FIG. 1. The hemoglobin material is held within the walls.

During the insolubilization process, using the preferred polyurethane matrix, the amount of $CO_2$ liberation can be varied over a very wide range. When $CO_2$ liberation is abundant, the resultant material is highly reticulated and spongy as illustrated in FIGS. 1-3. High flow rates are typical with such reticulated forms.

When formulated with a minimum of $CO_2$ liberation, polyurethane gels can be formed without reticulation. For a typical insolubilization of hemoglobin, the procedure would be:

(1) Pack red blood cells by centrifugation.
(2) Wash cells twice with physiological saline and repack.
(3) Lyse with distilled water to a concentration of hemoglobin of about 125 mg/ml and adjust the pH to 6.0 with dilute HCl.
(4) Remove red cell membranes by centrifugation to save the hemoglobin solution.
(5) Mix 20 ml of hemoglobin solution with 4 ml HYPOL.
(6) Allow to form a non-reticulated gel at room temperature (20°-25° C.).

Figure 6:
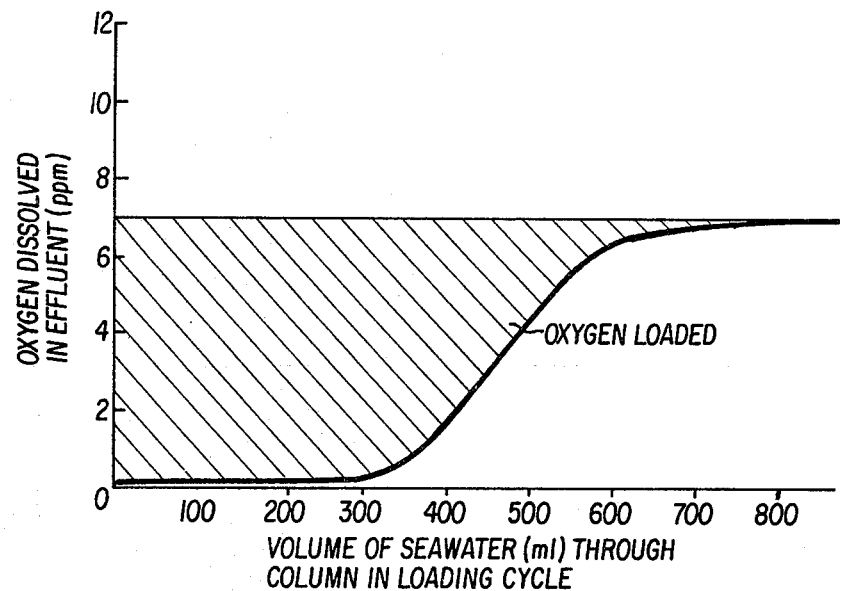
FIG. 6 is a representative oxygen loading curve.
Figure 8:
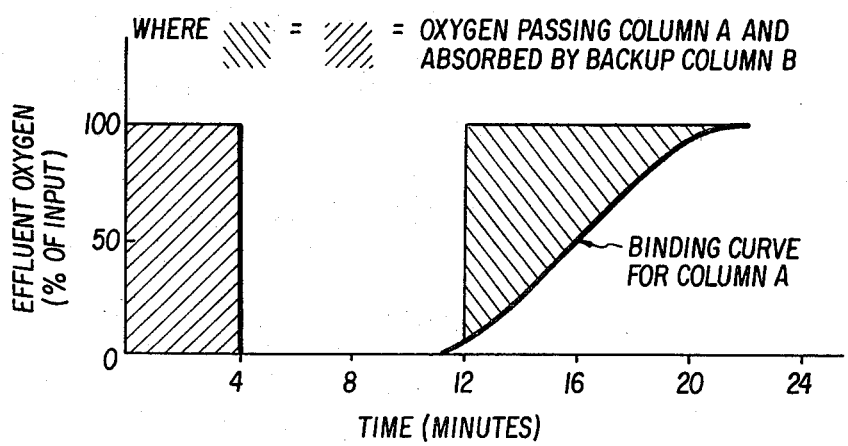
FIG. 8 is a representative absorption curve for a two column system.
Figure 7:
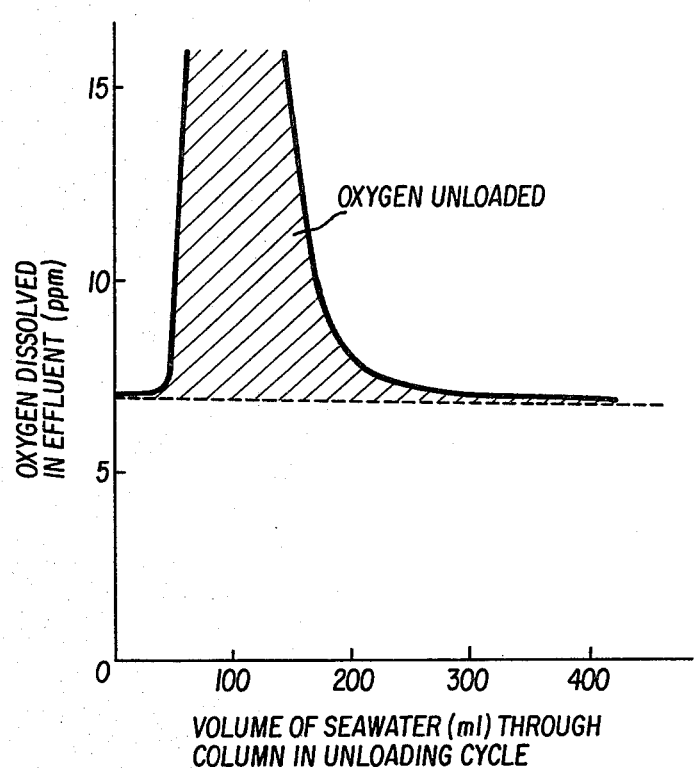
FIG. 7 is a representative oxygen unloading curve.

The resultant gel material can be ground and sorted into gel particles of defined size. Such gel particles of approximately 0.5 mm diameter have been found to have good diffusional and flow-rate characteristics. Good oxygen loading curves as shown in FIGS. 6-7 have been obtained using packed gel particle columns at flow rates of about one column volume per minute in devices illustrated in FIG. 5. The diffusional characteristics of such columns have been found to be dependent upon gel size, and such gel size is readily optimizable. Additionally, the use of sized-gel particles allows the use of fluidized bed absorption, which greatly increases the flow rate of oxygen-containing water. Furthermore, hemoglobin can be loaded into the sized-gel particles at high concentrations. Up to 30 g hemoglobin/1000 ml of column volume can be attained without problems with flow rates or diffusional difficulties. Overall yield of oxygen from such columns gives about 50-70% of the theoretical maximum based on the amount of insolubilized hemoglobin which the column contains. The pH during gel formation is quite important. The optimum pH for the insolubilization process appear to be about pH 6.

Hemoglobin and other oxygen carriers may be insolubilized at high concentration and with reversible oxygen binding characteristics in other than polyurethane matrices. Acrylic gels may also be used in this invention, especially the hydrophilic acrylates. Also reactive polymers containing maleic anhydride as one of the constituents are highly suitable for covalently binding hemoglobin or alternate oxygen carriers. Such polymers give high bonding yields (1 gr/gr polymer) and the resulting material exhibits reversible oxygen binding/unloading. These polymers are particularly suitable in the form of macroporous beads. Two other reactive polymers which may be used are the epoxy type, made by polymerization of glycidyl methacrylate as a copolymer, and the glutaronic aldehyde type, from pyridine-containing polymers reacted with cyanogen bromide. Additionally, hemoglobin and other oxygen carriers can be covalently bound to various insoluble matrices by other techniques, such as those used for enzyme immobilization, such as are described in Methods in Enzymology, Volume 44, Immobilized Enzymes, Academic Press, New York (1976). In these alternative methods of insolubilization, successful formulations must have the characteristics of durability, resistance to biodegradation, high specific density of hemoglobin on the carrier, high flow rates with little pressure drop, and good diffusional characteristics. Thus, Sephadex or Sepharose bound hemoglobin forms previously described are inferior methods for hemoglobin insolubilization.

Hemoglobin is, of course, by far the most common oxygen carrying protein found in nature. Within this context, however, it is possible to use in commercial applications any of the hemoglobins which are available in large quantity, e.g., human, bovine, porcine and equine hemoglobins. Further, whole blood, lysed cells, stripped or unstripped hemolysates can be used. Modified forms of hemoglobin, i.e. high or low affinity hemoglobins, as known in the art, are also useful. Hemoglobin can be treated to manipulate its affinity. Covalent or chemical modification, prior to immobilization, or treatment of the immobilized hemoglobin with cofactors that bind tightly and alter oxygen binding affinity (these are removable by washing the polymeric matrix with appropriate buffers) can be used. Additives, like catalase, superoxide dismutase and methemoglobin reductase, can be added to the solutions of hemoglobin prior to insolubilization in the polymeric matrix. These agents are normally found in red blood cells and can be useful in conferring structural and functional stability to the insolubilized hemoglobin. Additionally, reagents such as glycerol, which are known to impart structural stability to proteins in solution, can be usefully added to the solution of hemoglobin prior to incorporation into the polymeric matrix or, likewise, prior to covalent attachment to other polymeric supports.

Although hemoglobin is by far the most common oxygen carrier found in nature, other types of oxygen carriers are found in a number of species. In particular hemocyanin and hemerythrins are known and useable although they suffer from the deficiency of being unavailable in large quantities.

The use of synthetic oxygen carriers, such as the modified hemes described earlier and other like compounds known in the art, which show reversible oxygen binding, allow the attainment of high oxygen absorbing capacity in minimum absorber volume. These compounds are particularly useful when covalently bound to a polymeric matrix.

Figure 4:
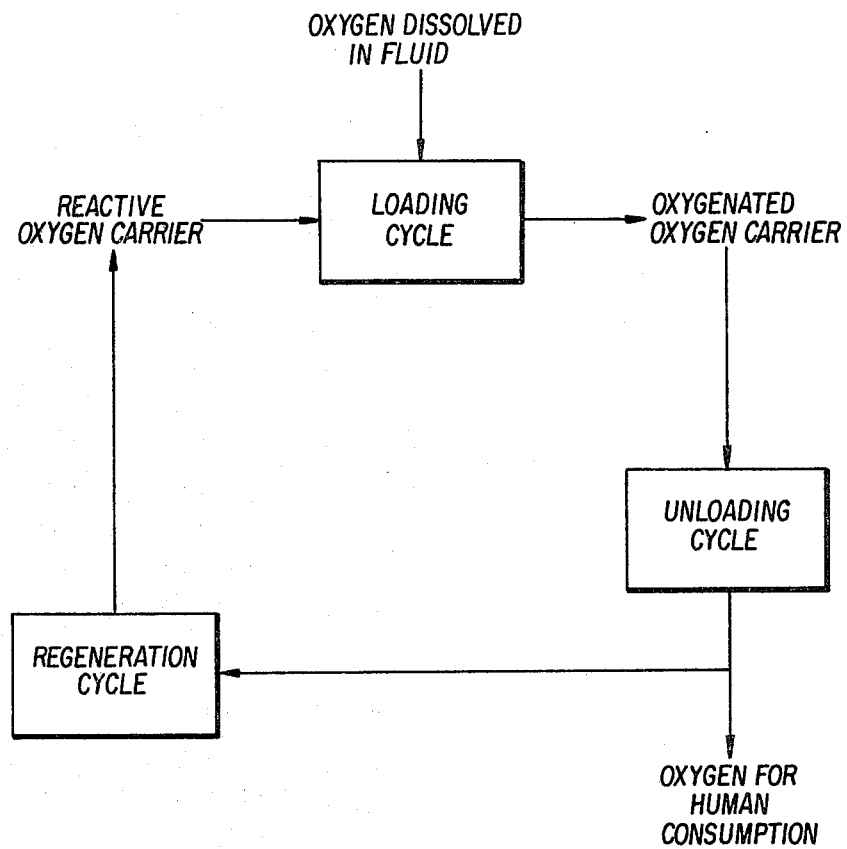
FIG. 4 is a schematic diagram of an oxygen extraction process.

While mere contact with dissolved oxygen is sufficient for oxygen loading of the oxygen carriers of this invention,, many variations are possible in the unloading cycle. A chemical alteration which oxidizes or inactivates the oxygen carrier is able to cause release of all of the bound oxygen. For example, ferricyanide oxidation of hemoglobin to the ferric state, called in the literature methemoglobin, is a chemical means for unloading the absorbed oxygen. The pertinent equations are:

$$Hb^{FeII} + O_2 \rightleftharpoons Hb^{FeII}O_2 \qquad (1)$$

$$Hb^{FeII}O_2 + \text{oxidant} \rightarrow Hb^{FeIII} + O_2 \quad (2)$$

$$Hb^{FeIII} + \text{reductant} \rightarrow Hb^{FeII} \quad (3)$$

where $Hb^{FeII}$ is ferrous deoxy hemoglobin, $Hb^{FeII}O_2$ is ferrous oxy hemoglobin and $Hb^{FeIII}$ is ferric (met hemoglobin. In this and other chemical methods, it is necessary to use a regeneration cycle to reactivate the oxygen carrier. With hemoglobin, dithionite can be used to reduce the active sites and render them reactive towards oxygen once again. The loading, unloading and regeneration cycles are shown in FIG. 4. During the unloading cycle, it is advantageous that the quantity of fluid used for regeneration, e.g. Ferricyanide solution, be appreciably less than is required for the loading process. The volume required in the loading process is, however, fixed by the concentration of dissolved oxygen in the fluid being processed.

Hemosponge incorporating fish hemoglobins can be used to extract oxygen from seawater. Its operation on the unloading cycle can be based on the pH sensitivity of specific fish hemoglobins. irreversible binding of specific cofactors to normal human blood can also render human hemoglobin pH sensitive so that pH changes can lead to oxygen unloading with this system as well. The cycle for oxygen release and reloading in these systems is depicted by the following equation:

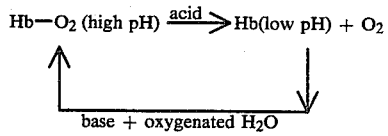

Figure 12:
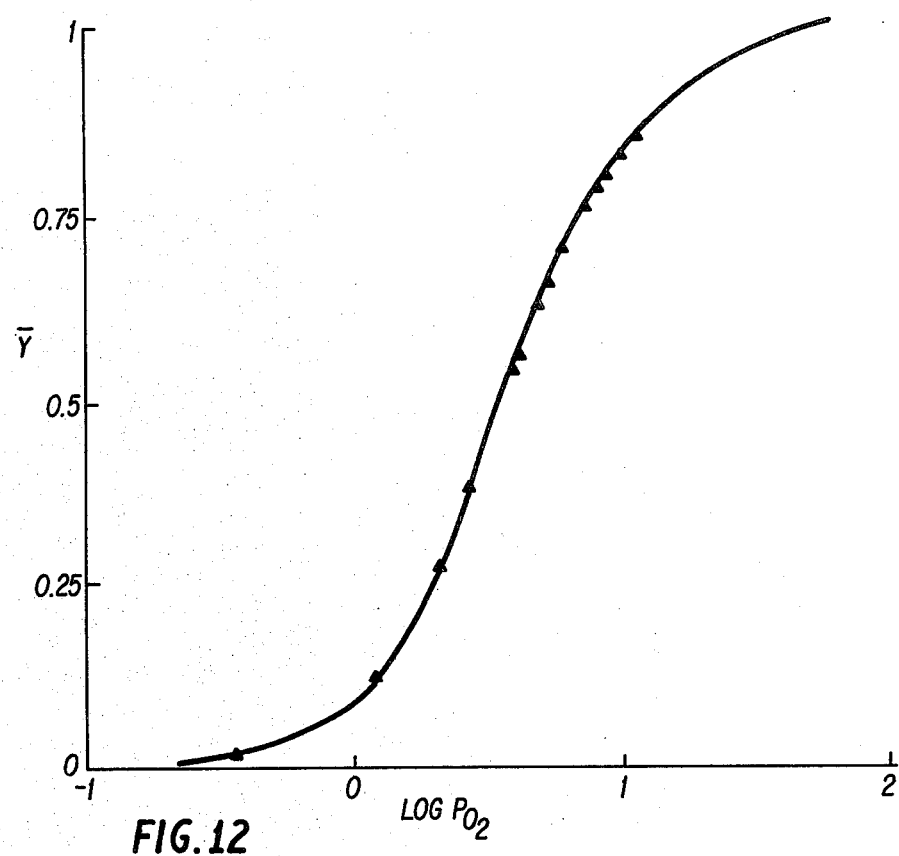
FIG. 12 depicts reversible oxygen binding by human hemoglobin in polyurethane gel particles of sizes comparable to those of red blood cells. Y represents fraction saturation of the oxygen carrier.

The unloading process need not require a chemical treatment. Simply decreasing the oxygen pressure in the environment of the insolubilized oxygen carrier is a highly practical approach to oxygen unloading. This is, in fact, the basis for oxygen unloading in physiological systems. From this it is apparent that the insolubilized oxygen carriers can function as blood substitutes if prepared at the same size as red blood cells. Reversible oxygen binding by particles of $10\mu$ average diameter which contain insolubilized hemoglobin in polyurethane is illustrated in FIG. 12 and Example 3. Similarly, drained columns or beds containing insolubilized oxygen carriers can be evacuated and the bound oxygen released by pulling a vacuum above the material and thus reducing the oxygen pressure. In laboratory tests, more than 50% of the loaded oxygen on insolubilized hemoglobin in polyurethane gels was found to be removed by this simple procedure. In the absence of a chemical unloading step the system requires no regeneration. The system can then be repetitively cycled between its loaded and unloaded conditions. Occasionally, regeneration steps using bacteriocides and reducing agents can be useful in keeping the system in useful operating condition. The possibility of carrying out such steps by methods of this invention is a major advantage over previous art relative to oxygen extraction from gases.

A practical system may be based on a procedure whereby a fully loaded gel is evacuated and the gas is released from the gel and is then pumped directly to oxygen storage devices. A mist separator can be useful in this step. The efficiency of the unloading cycle can be improved by bleeding low pressure steam through the system to further lower the oxygen pressure and simultaneously decrease the oxygen affinity of the insolubilized oxygen carrier.

Unloading with or without a chemical unloading step can also be effected indirectly through a semipermeable membrane. In this case, fluid of low oxygen content or with a chemical which causes oxygen to be released is circulated through the fully loaded bed of absorbent and then cycled through a tubular bundle of selectively permeable membranes. A pump on the other side of the membrane can be utilized to drive the released oxygen out of the circulating fluid and across the semipermeable membrane into an oxygen storage chamber.

This invention has two main features. First, the invention involves biologically active hemoglobin or other oxygen carriers in polymeric matrices, creating what is referred to as Hemosponge. Second, the invention involves creation of a process, based on the Hemosponge, to provide for oxygen extraction from fluids, such as water or air, for human respiratory needs.

A major improvement of this invention is the simplicity of the process by which hemoglobin and appropriate cofactors or blood or blood products can be insolubilized at high concentration and maintained in an active and readily useful state. Since polyurethane is the preferred matrix material, methods for Hemosponge preparation in this form are described in detail, as follows. Hemosponge is prepared by making an aqueous solution or suspension of the biological material to be entrapped, mixing it with a non-ionic detergent of low toxicity, and then mixing the aqueous phase with a prepolymer of urethane which has the characteristic of being water soluble. Alternatively, the protein can be lyophilized and dispersed in the dry phase prior to mixing with aqueous phase. Very high final protein concentrations can be achieved in this way. A number of parameters can be varied by the fabricator in preparation of specific Hemosponge products. Insofar as the physical nature of the polyurethane foam is concerned, the variable parameters and their effect have been described in large part by W. D. Grace and Co., the manufacturer of the hydrophilic prepolymer, in a technical brochure entitled "HYPOL Foam Polymer—What it is and what it does:". As has been mentioned, the HYPOL prepolymer contrasts with conventional (hydrophobic) foam preparations, where 3 to 5 parts of water are used per 100 parts of polymer. The amount of water used with HYPOL hydrophilic foam polmer does not have to be carefully adjusted to the approximate stoichiometric equivalent of isocyanate content. Instead, a broad range of water to prepolymer ratios may be used—from 2,000 to 20,000 percent of the theoretical amount required. Preferably, 35 to 200 parts of water per 100 parts of prepolymer are used, depending on the foam characteristics desired. Both cell structure and aesthetic properties of foams produced from HYPOL prepolymer can be controlled by changing the amount of water, type of surfactant, etc. For example:

1. Foams ranging from cosmetic softness to rigid and from conventional open cell structure to fully reticulated.
2. Rapidly wetting to slow, controlled wetting foams can be formed. Such foams absorb and retain from 10 to 30 times their weight of water.
3. Foams with densities of from 2 lbs./ft.$^3$ to 20 lbs./ft.$^3$ can be readily prepared from HYPOL prepolymer. Tensile properties are generally comparable to those of conventional polyurethane.

In addition to these features, the HYPOL Foams have been shown to have fire retardant properties vastly superior to those of conventional foams. Furthermore, favorable results from toxicity tests on HYPOL have been reported. At appropriate levels, no deaths or adverse symptoms were noted in animal inhalation, ingestion and dermal studies. This feature is considered relevant insofar as particles of immobilized hemoglobin of 5-10 microns diameter may be useful as blood substitutes as illustrated in Example 3.

Insofar as Hemosponge requires the addition of biologically active materials to the aqueous phase prior to polymerization, a few additional variables are introduced relative to the process to be followed. These include (a) the nature of the biological material (or materials), (b) the concentration of the biological material in the aqueous phase, (c) the presence or absence of dispersing agents or detergents with the biological material, which affects the dispersal of the biological material in addition to its effect on the uniformity of the cell structure and cell size of the polyurethane foam, and (d) the ratio of aqueous phase to dry phase whereby the retention of the biological material in the foam can be regulated. Variables which can be set by the fabricator include the following:

Nature of biological material and concentration per gram of monomer
Temperature of reaction
Pressure during the reaction
Presence or absence of specific detergents or dispersal of the biological material in the water soluble monomer.
Presence or absence of stirring during the process of catalysis
Degrees of agitation during catalysis
pH of catalysis (this is subject to a limited amount of control)
Presence of single or multiple substances in the monomer prior to catalysis
Absolute volume of reaction mixture
Ratio of catalyst to monomer solution In order to clarify the exact nature of the Hemosponge, in its preferred embodiment, reference will be made to photographs of Hemosponge taken with a scanning electron microscope. FIGS. 1, 2 and 3 exemplify the formation typical when there is human hemoglobin in the aqueous phase. For formation of Hemosponge the conditions and cofactors can be varied to suit particular physical needs. A formulation illustrative of typical formulations is:

Aqueous Phase (a) 8 ml of Hemoglobin (50 mg protein/ml of H2O). The concentration of hemoglobin is not critical and can vary from 1 mg/ml to 150 mg/ml or even higher. The hemoglobin can be from humans or nonhumans.
(b) 5 ml distilled water.
(c) 1 ml F-68 (19% by weight in aqueous solution) F-68 is a non-ionic detergent of proven low toxicity; produced by BASF Wyandotte Corporation of Wyandotte, Michigan. The presence of detergent is to achieve good reticulation. If non-reticulated foams or if gels are to be made, no detergent is needed. Non-ionic detergents, like Tween or Triton, can be substituted for the F-68. The concentration of detergent is not critical.

Dry Phase (a) 6 g FHP-2000 Hypol Hydrophilic Prepolymer. Hypol is a foamable hydrophilic polyisocyanate manufactured by W. R. Grace and Co., of Cambridge, Mass. Similar formulations are obtained with FHP-2001, FHP 3000 and FHP 3001 prepolymers. Nonfoaming Hypol pre-polymers can also be used.

The aqueous and dry phase materials are manually stirred with a glass stirring rod for about 15 seconds. Mixing is carried out under a vacuum hood. The polymerization, carried out at room temperature, is completed in about 3 minutes and the temperature during the foaming does not exceed 35° C. After the polymerization is complete, the product is rinsed with distilled water to remove excess detergent and unreacted material.

FIG. 1 is a 40× magnification showing the nature of the matrix in which the biologically active material, human hemoglobin, in this case, is incorporated. It shows the highly vesicular nature of the sponge, its thin walls, and the many holes which allow fluids to flow readily between and through compartments. FIG. 2 shows a 2400× magnification of the thin walls of the sponge at a region of contact between two of the oval compartments. Closer examination of the surface of the walls reveals a rippled surface. This is shown in FIG. 3 in a photograph at 4000× magnification. The biological material is held within the walls.

Figure 5:
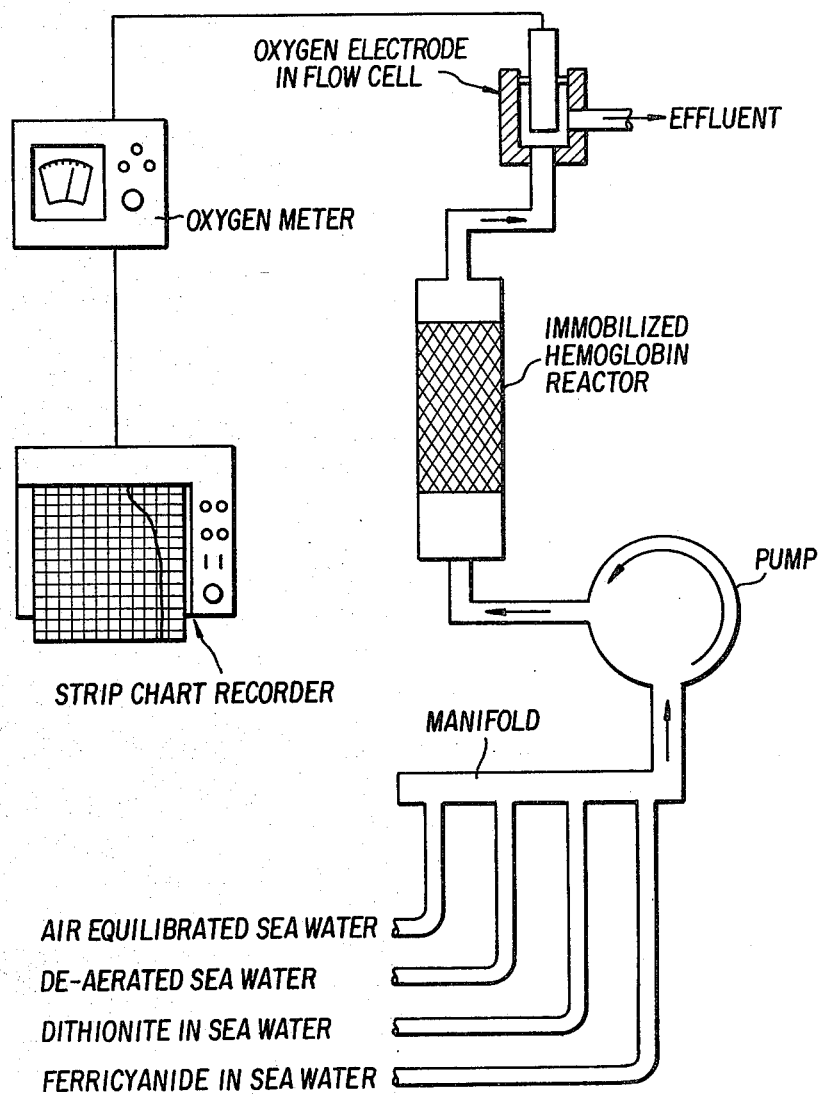
FIG. 5 is a schematic diagram of a laboratory oxygen recovery apparatus.

FIG. 5 and FIGS. 9-11 show schematic diagrams of various laboratory devicesus wherein the oxygen loading and unloading process can be carried out by making use of insolubilized hemoglobin or other oxygen carriers. In particular, the apparatus of FIG. 5, for oxygen extraction from seawater, comprises a manifold wherein various solutions (air-equilibrated seawater, deaerated seawater, dithionite in seawater and ferricyanide in seawater) can be fed to a pump. The pump feeds the solution to a reactor containing the immobilized hemoglobin. This reactor can be of the packed bed or fluidized bed type. Effluent from the reactor is discharged through a flow cell containing an oxygen electrode whereby the concentration of dissolved oxygen in the effluent can be determined. The oxygen concentration can be read directly from an oxygen meter and/or recorded on a strip chart recorder. Typical oxygen loading and unloading curves for the apparatus of FIG. 5 are shown in FIGS. 6 and 7. FIG. 7 shows a plot of dissolved oxygen in the effluent as a function of the amount of air-equilibrated seawater (7 ppm dissolved oxygen content) passed through the reactor during the loading cycle. FIG. 7 shows a plot of dissolved oxygen in the effluent as a function of the amount of ferricynaide/seawater solution (7 ppm dissolved oxygen content) passed through the reactor during the loading cycle.

Using the typical experiment illustrated previously, we can make some calculations based on the use of a twostage two column model. To do this we can examine the time sequence of the loading of a single column. Consider FIG. 8. After a column (column A) reaches the point at which significant oxygen is found in the effluent (12 minutes as shown in the diagram) second column (column B) would be added down-stream from column A. Flow of seawater is now through both columns in sequence until column A is saturated (20 minutes in the diagram). At this point, column A is removed and unloaded while column B continues on line.

During the period (12 to 20 minutes) that column B has been acting as a back-up column it has picked up the amount of oxygen indicated by the lined area in the diagram. This is equivalent to the amount of oxygen in the cross-hatched area of the diagram and so column B is loaded to the extent that it would have been if it had been a primary column for 4 minutes. Thus, the effluent from column B will contain significant oxygen 8 minutes after it has become the primary column. Column B will be saturated 16 minutes after becoming the primary column. The time sequence is then as follows:

| B | P | P | U | B | P | P | U | B | P | P | U | Column A |
| P | U | B | P | P | U | B | P | P | U | B | P | Column B |

Each block = 8 minutes

P = Primary column, first in series
B = Back-up column, second in series
U = Unload and regenerate Thus, the total amount of resin is loaded and unloaded every 32 minutes. Assuming 70% oxygen yield (based on the concentration of hemoglobin in the gel), 1 g of hemoglobin will deliver at each unloading $0.7 \times 1.4$ ml oxygen at 22° C., 760 torr = 1 ml delivered or, considering the 32 minute cycle, this will deliver 0.03 ml/min. Note that the above example of oxygen extraction utilizes sized gel particles in which human hemoglobin is used as the oxygen carrier. The apparatus for such extraction is shown in FIG. 5 and schematically in FIG. 9. Alternatively, the manifold of FIG. 5 can switch between solutions of air, low oxygen gas or vacuum or dithionite in 0.05 M Tris buffer or 0.2 M phosphate buffer, or ferricyanide solution in such buffers to accomplish oxygen extraction from air. The methodology as just described is therefore applicable for both oxygen extraction from water or from gas. A spectral demonstration that the insolubilized oxygen carrier, hemoglobin, in this example, can extract oxygen from air was obtained by spectrophotometric methods (see FIG. 13).

Figure 9:
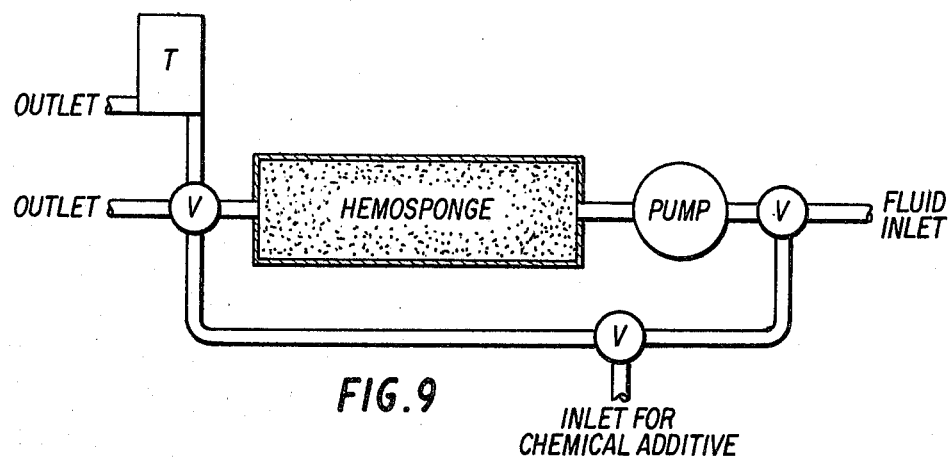
FIG. 9 is a schematic diagram of an absorption system utilizing a static oxygen carrier, denoted as Hemosponge.
Figure 10:
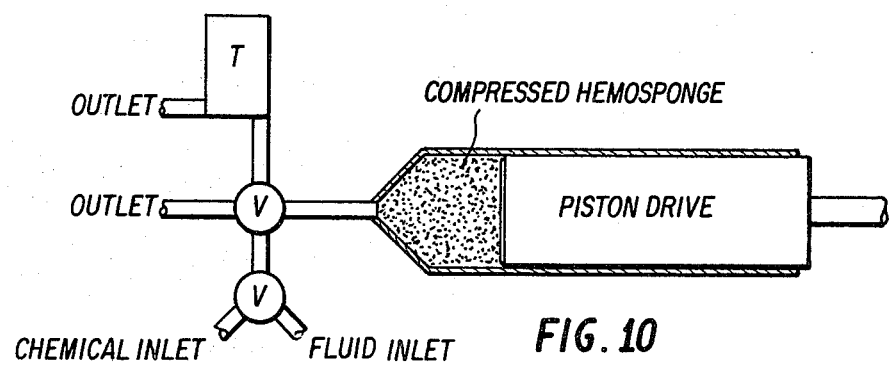
FIG. 10 is a schematic diagram of an absorption system utilizing a piston system capable of driving the fluid flow from the various inlets and compressing the static oxygen carrier, denoted as Hemosponge.
Figure 11:
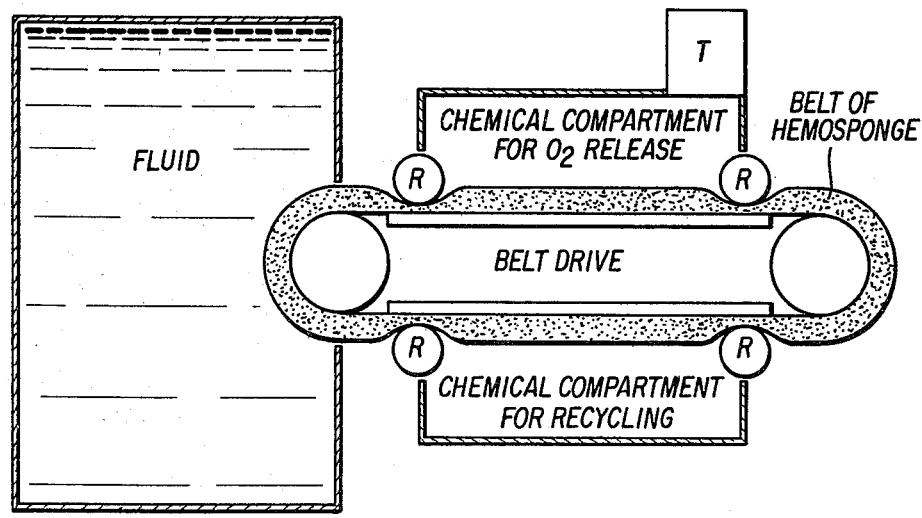
FIG. 11 is a schematic diagram of an absorption system utilizing a belt system wherein the oxygen carrier, denoted as Hemosponge, is not static but is transported from regions of high oxygen concentration to regions of low concentration or to a region where oxygen release is initiated by a chemical means.

FIGS. 9–11 illustrate additional mechanical embodiments for the oxygen extraction process. Thus the oxygen carrier can be static and various fluids can be flowed by it as shown in FIGS. 9 and 10. Otherwise, the oxygen carrier can be cycled between areas of high oxygen content, e.g., air or nautral waters, and areas where oxygen unloading is accomplished. This is schematically depicted in FIG. 11. The method of how the oxygen carrier can be moved from regions of high oxygen to regions where unloading is accomplished is elaborated by FIG. 12 and Example 3, where the carrier is shown to perform as a blood substitute.

As noted above, the extraction of oxygen from a fluid like air can also be effected using a device of the sort described herin. In this mode, the supported bed of the immobilized oxygen carrier is operated with air flowing through it, rather than water. The oxygen carrier will not only remove oxygen from the air, but, the gas, having the oxygen removed, will be greatly enriched in $N_2$ (see the table below)

| | % Composition | |
|---|---|---|
| Gas | Air | Air (quantitative removal of $O_2$) |
| $O_2$ | 21 | — |
| $N_2$ | 78 | 98.73 |
| Ar | 0.93 | 1.18 |
| other | 0.07 | 0.09 |

Figure 13:
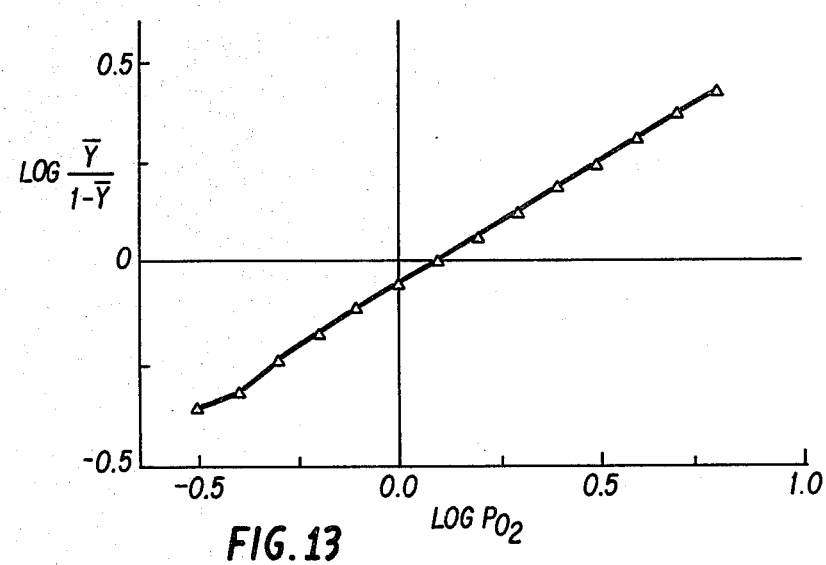
FIG. 13 shows a spectrophotometric demonstration of reversible oxygen binding by a film of hemoglobin insolubilized in a polyurethane gel. Oxygen extraction in this case is from air. Y represents fractional saturation of the oxygen carrier with oxygen.

A demonstration that the immobilized carrier is capable of extracting oxygen from air is clearly obtainable by spectrophotometric analysis as shown in FIG. 13. A film of insolubilized oxygen carrier, hemoglobin, in this case, was reversibly cycled between low and high oxygen concentration. The saturation of the carrier with oxygen was determined spectrophotometrically and from such measurements it is possible to determine loading-unloading characteristics of devices made of such films. In the example of FIG. 13, half saturation occurs at an oxygen pressure of 1.26 mm Hg. As noted previously, these characteristics are subject to modification by using different oxygen carriers or by chemically modifying human hemoglobin.

Having generally described this invention, a further understanding can be obtained by reference to certain specific examples which are provided herein for purposes of illustration only and are not intended to be limiting unless otherwise specified.

EXAMPLE 1

The following tables are those which represent measurements of the efficiency of an oxygen extraction device based on the piston system design of FIG. 10 in which the compressibility of a reticulated matrix of Hemosponge is utilized. In the example outdated human blood was used as the oxygen carrier in the Hemosponge and chemical recycling was carried out as in equations I–III. As is apparent, the additives co-incorporated with the blood in the reticulated matrix affect the efficiency of extraction.

| HEMOGLOBIN ADDITIVE | Wt. Nb | % $O_2$ IN GAS RECOVERED |
|---|---|---|
| 5% GLYCEROL | 3.5 GM | 23.4% |
| 10% GLYCEROL | 3.5 GM | 22.35 |
| CATALASE | 3.5 GM | 23.5% |
| CATALASE + 2% GLYCEROL | 3.5 GM | 22.1% |
| CATALASE, 2% GLYCEROL, and 5 mM INOSITOL HEXAPHOSPHATE | 3.5 GM | 21.7% |
| " | 7.0 GM | 27.1% |
| " | 10.0 GM | 23.6% |

EXAMPLE 2

This example illustrates the process and method whereby hemoglobin, an oxygen carrier, is bound to a support, that is not polyurethane, in high concentration and with biological activity such that oxygen extraction can be achieved.

A mixture of 7 g of tetraethylene glycol dimethacrylate, 2 g methacrylic acid, 1 g maleic anhydride, 0.1 g of azoisobutyronitrile was dissolved in 100 ml of benzene and warmed to 60° C. for 4 hours. Thereafter, 0.1 g of azoisobutyronitrile was added and the mixture was heated at 70° C. for 2 hours and then at 80° C. for 2 hours. The polymer which precipitated was filtered off, washed with petroleum ether and dried in a vacuum to give 8.5 g of polymer.

One gram of the polymer prepared by this procedure was mixed with 10 ml of a hemoglobin solution, containing 120 mg hemoglobin per ml and 20 ml of water. The pH was adjusted to 6.3 and maintained at pH of 6.3-6.5 by addition of NaOH. After 24 hours, the polymer bound hemoglobin was removed by filtration.

Hemoglobin in filtrate+washing: 72 mg
Hemoglobin bound to polymer: 1.13 g

The bound hemoglobin was reduced with dithionite and then oxygenated by bubbling air through a suspension thereof. It was then treated with excess potassium ferricyanide solution:

$O_2$ released=0.78 mg
Theoretical amount of $O_2$ bound by hemoglobin in polymer=1.92 mg
Yield=41%

EXAMPLE 3

This example illustrates the process and method whereby hemoglobin, an oxygen carrier, can be insolubilized in polyurethane particles of dimensions like those of red blood cells (5–10$\mu$) and perform as a blood substitute.

In this case, 20 ml of human hemoglobin at a concentration of 125 mg/ml was mixed with 4.0 ml of HYPOL (Grace Co.) non-foaming prepolymer and allowed to polymerize at room temperature as a gel. The gel was ground to provide particles and then sized. Such particles in the size range of about 0.5 mm were used in columns for oxygen extraction from seawater as described in detail in the text (FIG. 5). Smaller particles were obtained by repetitive screening and preparative centrifugation. Particles with dimensions comparable to those of red blood cells (5–10$\mu$) were obtained and the oxygen binding properties of such particles, in 0.2 M phosphate buffer, pH 7.0, at 20° C., were examined. FIG. 12 illustrates an oxygen binding curve for such particles and demonstrates that such may be considered as blood substitutes. Thus, for the insolubilized hemoglobin in small particles, it was found that half saturation was attained at an oxygen pressure of 3.7 mm Hg and cooperativity, expressed by the Hill coefficient, was 1.7. In human hemoglobin, in solution under comparable conditions of temperature, buffer and pH, the oxygen pressure for half saturation was 2.4 mm Hg and cooperativity was expressed by a Hill coefficient of 2.5.

Having now fully described this invention, it will be apparent to one of ordinary skill in the art that many changes and modifications can be made thereto without departing from the spirit or scope of the invention set forth herein.

We claim:

1. An oxygen carrier, capable of reversibly binding and releasing oxygen, immobilized in a polymer matrix selected from the group consisting of compounds having urethane linkage, acrylic gels, maleic anhydride containing polymers, epoxy type polymers, glutaronic aldehyde type polymers and mixtures thereof.

2. The immobilized oxygen carrier of claim 1, wherein said oxygen carrier is hemoglobin, a hemocyanin a synthetic heme, an organo-metallic compound or a chemically modified hemoglobin or hemocyanin.

3. The immobilized oxygen carrier of claim 1, wherein said polymer matrix is a hydrophilic acrylate gel.

4. The immobilized oxygen carrier of claim 1, wherein said polymer matrix is a polyurethane.

5. The immobilized oxygen carrier of claim 4, wherein said polyurethane is a foam.

6. The immobilized oxygen carrier of claim 4, wherein said polyurethane is a gel.

7. The immobilized oxygen carrier of claim 6, wherein said polyurethane gel is in the form of sized gel particles.

8. The immobilized oxygen carrier of claim 7, wherein said sized gel particles have a diameter in the range of about 5 to 10 microns.

9. The immobilized oxygen carrier of claim 1, wherein said oxygen carrier is hemoglobin.

* * * * *